(12) United States Patent
Sethi

(10) Patent No.: US 12,702,337 B1
(45) Date of Patent: Aug. 11, 2026

(54) METHODS AND DEVICES FOR MONITORING BRAIN FUNCTIONS BY MAGNETIC FIELD MEASURING OF MEG SIGNAL VIA AN EAR CAVITY

(71) Applicant: TDK Corporation, Tokyo (JP)

(72) Inventor: Rakesh Sethi, San Jose, CA (US)

(73) Assignee: TDK Corporation, Tokyo (JP)

(*) Notice: Subject to any disclaimer, the term of this patent is extended or adjusted under 35 U.S.C. 154(b) by 0 days.

(21) Appl. No.: 19/229,473

(22) Filed: Jun. 5, 2025

Related U.S. Application Data

(63) Continuation of application No. 17/569,196, filed on Jan. 5, 2022, now Pat. No. 12,521,053.

(51) Int. Cl.
*A61B 5/245* (2021.01)
*A61B 5/00* (2006.01)
*A61B 5/246* (2021.01)

(52) U.S. Cl.
CPC .............. *A61B 5/245* (2021.01); *A61B 5/246* (2021.01); *A61B 5/6817* (2013.01); *A61B 5/7203* (2013.01); *A61B 2562/18* (2013.01)

(58) Field of Classification Search
CPC ....... A61B 5/245; A61B 5/246; A61B 5/6817; A61B 5/7203; A61B 2562/18
See application file for complete search history.

(56) References Cited

U.S. PATENT DOCUMENTS

| | | | | |
|---|---|---|---|---|
| 2008/0084204 | A1 | 4/2008 | Seki et al. | |
| 2009/0299215 | A1 | 12/2009 | Zhang | |
| 2019/0174237 | A1 | 6/2019 | Lunner et al. | |
| 2021/0240433 | A1 | 8/2021 | Sato et al. | |
| 2023/0210425 | A1* | 7/2023 | Sethi ...................... | A61B 5/245 600/409 |

OTHER PUBLICATIONS

Sosa et al (Human ear tympanum oscillation recorded using a magnetoresistive sensor, Rev. Sci. Instrum. 73, 3695-3697 (2002).*

* cited by examiner

*Primary Examiner* — Serkan Akar
(74) *Attorney, Agent, or Firm* — Morgan, Lewis & Bockius LLP

(57) ABSTRACT

An example device includes a first magnetoresistance sensor configured for detecting magnetoencephalography (MEG) signals from a first ear cavity of a user. The example device also includes a first enclosure configured to magnetically shield the first magnetoresistance sensor. The first magnetoresistance sensor is positioned entirely within the first enclosure, and the first enclosure has an opening through which the first magnetoresistance sensor is configured to detect the MEG signals propagated from the user to the opening of the first enclosure. The example device further includes circuitry coupled to the first magnetoresistance sensor and configured to monitor brain function of the user based on the MEG signals. Methods for detecting a magnetic field from an ear cavity with a magnetoresistance sensor are also disclosed.

12 Claims, 4 Drawing Sheets

METHODS AND DEVICES FOR MONITORING BRAIN FUNCTIONS BY MAGNETIC FIELD MEASURING OF MEG SIGNAL VIA AN EAR CAVITY

TECHNICAL FIELD

This application relates generally to electromagnetic measurements and analysis, including methods and devices for monitoring cognitive brain function via electromagnetic measurements from an ear cavity.

BACKGROUND

Enhancements in sensor technologies have led to improved diagnostics for medical purposes. For example, various imaging techniques, such as ultrasound imaging, x-ray imaging, computed tomography, and magnetic resonance imaging (MRI), have enabled diagnosis that was not possible without such imaging techniques. Non-imaging techniques, such as electrocardiogram, are also widely used.

SUMMARY

Brains, which provide vital functions, are protected anatomically and biochemically. For example, the cranium, surrounding a brain, protects the brain from mechanical impacts. Although non-invasive imaging techniques (e.g., MRI, including functional MRI) are used to observe the spatial aspects of the brain (e.g., the structure of the brain and the distribution of certain substances within the brain), direct probing of brains can be challenging.

The devices and methods described herein address challenges associated with conventional devices and methods for analyzing the brain function. Instead of direct probing of a brain, electrical or magnetic signals measured adjacent to the brain may contain information associated with the brain function. For example, as described herein, the electrical or magnetic signals measured from an ear canal may contain information indicating the cognitive load of a subject. In addition, the electrical or magnetic signals measured from the ear canal may also contain information indicating physiological function of other organs (e.g., organs other than the ear and the brain).

The disclosed devices may replace conventional devices or, when used in conjunction, provide additional information, which can further improve medical diagnosis. For example, the disclosed devices and methods may be used for diagnosis or prognosis of dementia or Alzheimer's disease. The disclosed devices and methods may also be used with healthy subjects. For example, the disclosed devices and methods may be used to assess athletic abilities of athletes and other healthy subjects.

In accordance with some embodiments, a device includes a first magnetoresistance sensor for detecting a magnetic field from a first ear cavity.

In accordance with some embodiments, a method includes placing a first magnetoresistance sensor adjacent to a first ear cavity; and detecting a magnetic field from the first ear cavity.

BRIEF DESCRIPTION OF THE DRAWINGS

The disclosed devices and methods allow electromagnetic measurements from ear cavities, which may also provide information about organs other than ears.

For a better understanding of the various described embodiments, reference should be made to the Description of Embodiments below, in conjunction with the following drawings in which like reference numerals refer to corresponding parts throughout the figures.

DESCRIPTION OF EMBODIMENTS

Reference will be made to embodiments, examples of which are illustrated in the accompanying drawings. In the following description, numerous specific details are set forth in order to provide a thorough understanding of the various described embodiments. However, it will be apparent to one of ordinary skill in the art that the various described embodiments may be practiced without these particular details. In other instances, methods, procedures, components, circuits, and networks that are well-known to those of ordinary skill in the art are not described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first sensor could be termed a second sensor, and, similarly, a second sensor could be termed a first sensor, without departing from the scope of the various described embodiments. The first sensor and the second sensor are both sensors, but they are not the same sensor.

The terminology used in the description of the embodiments herein is for the purpose of describing particular embodiments only and is not intended to be limiting of the scope of claims. As used in the description and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1:
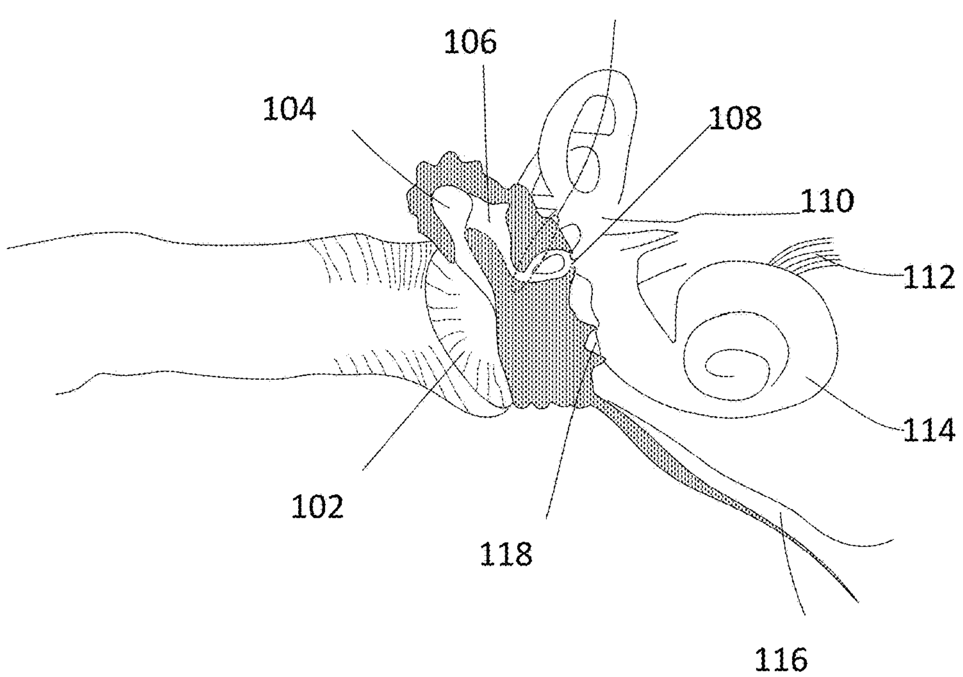
FIG. 1 is a schematic diagram illustrating a middle ear and an inner ear.

FIG. 1 is a schematic diagram illustrating a middle ear and an inner ear (of a human). Shown in FIG. 1 are tympanic membrane 102 (also called an eardrum), malleus 104, incus 106, and stapes 108. Tympanic membrane 102 separates the middle ear from the external ear. Malleus 104, incus 106, and stapes 108 (coupled to the oval window) are bones that transfer the vibration of tympanic membrane 102 to the inner ear. FIG. 1 also shows vestibular nerve 110, cochlear nerve 112, cochlea 114, Eustachian tube 116, and round window 118. Vestibular nerve 110 is part of the vestibular system, transmitting sensory information associated with gravity and linear acceleration. Cochlear nerve 112 transmits auditory sensory information from cochlea 114 to the brain. Eustachian tube 116 is a tube that connect the nasopharynx to the middle ear. Round window 118, sealed by the round window membrane, vibrates in conjunction with vibrations entering the inner ear through the oval window (typically in an opposite phase), thereby moving fluid in cochlea 114 to move. Also shown in FIG. 1 is a stapedius muscle 120 (also called stapedius), which stabilizes stapes 108.

Figure 2:
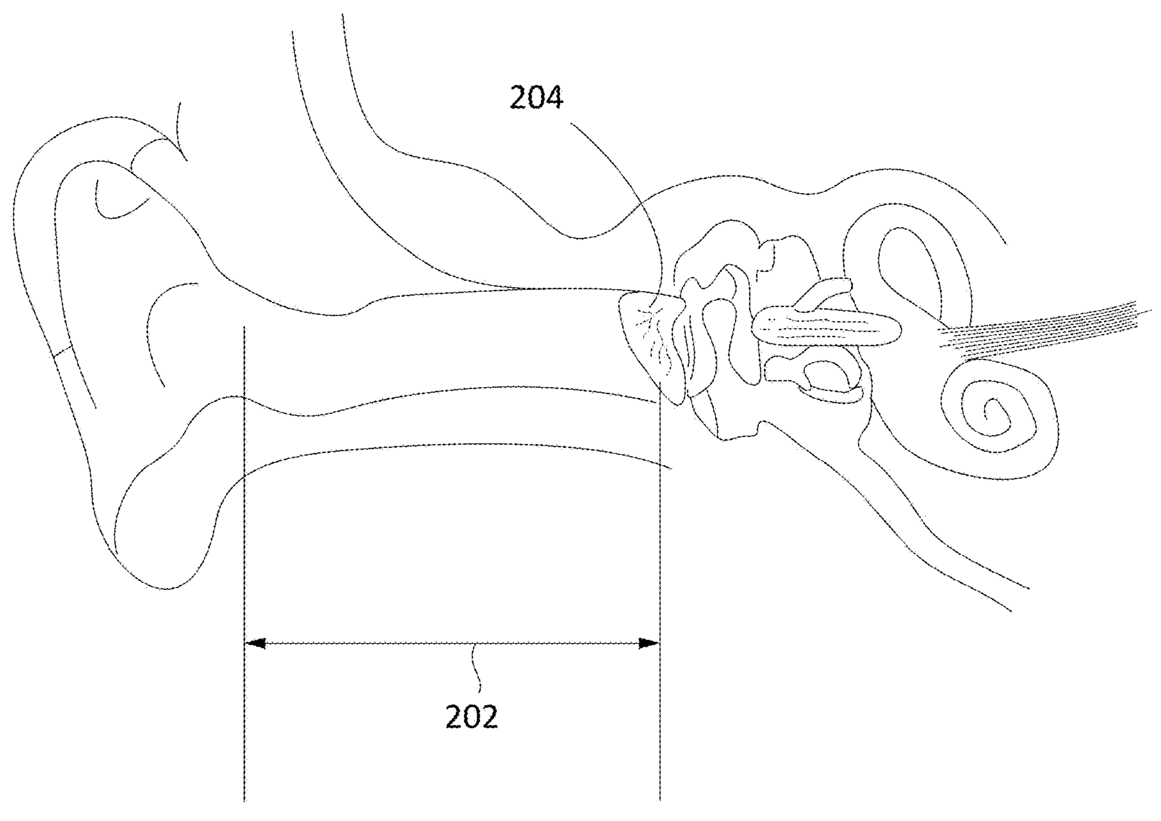
FIG. 2 is a schematic diagram illustrating an ear cavity.

FIG. 2 is a schematic diagram illustrating an ear cavity 202 (also called external auditory canal) between the tympanic membrane 102 (e.g., eardrum) and the outer ear. In the ear cavity 202 (also called herein an ear canal), the magnetoencephalographic signals can be obtained due to the proximity between the ear canal and the brain. In addition, it is possible to perform magnetocardiography measurements due to the presence of arteries (e.g., external carotid artery and auricular arteries) adjacent to the ear canal. Furthermore, a sensor (or a sensor assembly) located in the ear canal may also detect auditory signals.

Figure 3A:
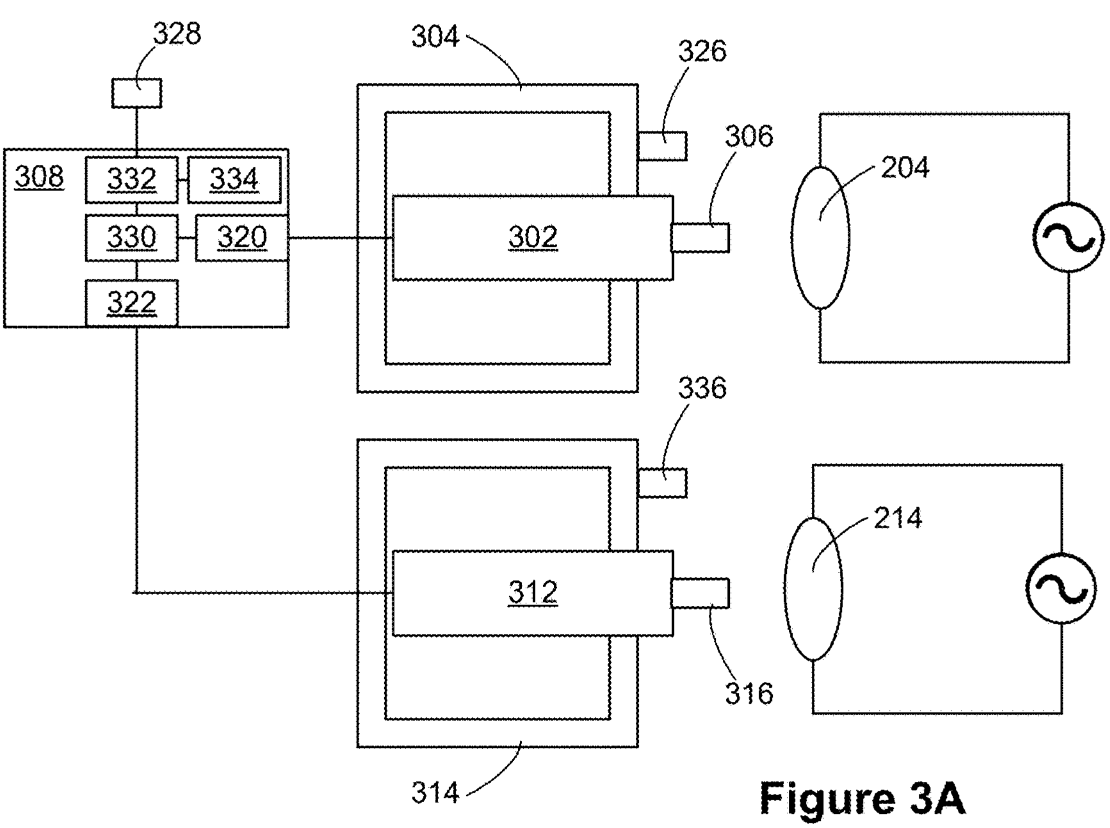
FIGS. 3A and 3B illustrate devices for electromagnetic measurements in accordance with some embodiments.
Figure 3B:
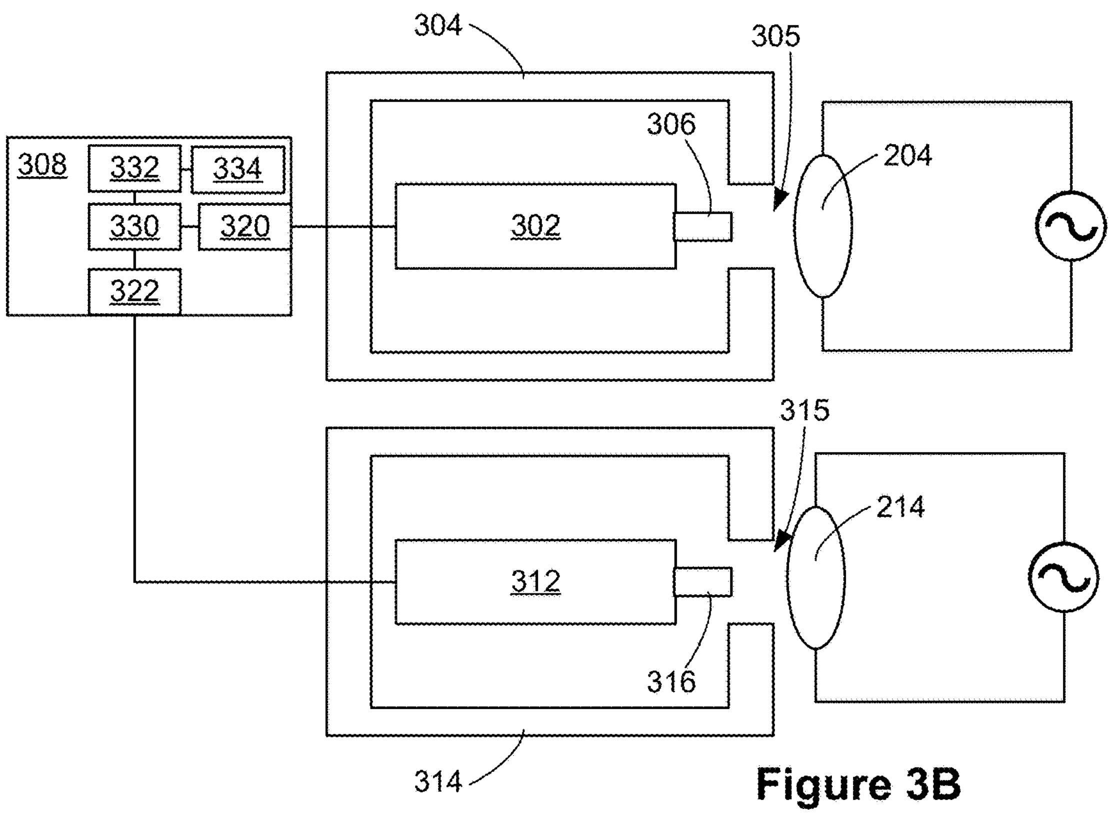

FIGS. 3A and 3B illustrate devices for electromagnetic measurements in accordance with some embodiments. In some embodiments, such devices include a magnetic field sensor (e.g., magnetic field sensors 302 and 312). For example, the magnetic field sensors 302 and 312 may detect magnetic signals (e.g., biomagnetic signals) using magnetoresistance (e.g., using a magnetoresistance sensor). Such magnetic field sensors 302 and 312 may operate at room temperature, without requiring ultra-low temperature, which is typically required for superconducting quantum interference device (SQUID) sensors. Thus, such magnetic field sensors 302 and 312 allow fabrication of compact and portable devices for measuring magnetic signals from human subjects. In some configurations, such magnetic field sensors 302 and 312 are included in headsets.

As explained above, measuring the magnetic field from the ear cavity 202 can provide information associated with the brain. In FIGS. 3A and 3B, the ear of a subject is illustrated as an equivalent circuit containing the tympanic membrane 204 (or 214) and an oscillator. The electromagnetic field from the subject may be transmitted through, or propagated from the direction of, the tympanic membrane 204 (or 214).

As shown in FIGS. 3A and 3B, a magnetic shielding enclosure (e.g., enclosures 304 and 314) is used to reduce noise associated with environmental magnetic field. In some embodiments, the magnetic shielding enclosure includes a conductive or magnetic material (e.g., in the shape of sheet metal, metal screen, or metal foam), such as copper, brass, nickel, silver, steel, and tin.

In some configurations, the magnetic field sensors are at least partially located outside the enclosures (e.g., in FIG. 3A, the magnetic field sensor 302 is located outside the enclosure 304 and the magnetic field sensor 312 is located outside the enclosure 314). These configurations allow the magnetic field sensors to be placed at least partly within the ear cavity 202, and thus, enhance the strength of the magnetic signal detected by the magnetic field sensors.

In some other configurations, the magnetic field sensors are located entirely within the enclosures (e.g., in FIG. 3B, the magnetic field sensor 302 is located entirely within the enclosure 304 and the magnetic field sensor 312 is located entirely within the enclosure 314). In such configurations, the enclosures have openings 305 and 315 to allow magnetic field to enter the enclosures so that the magnetic field can be detected by the magnetic field sensors located within the enclosures.

In some embodiments, the magnetic field sensors 302 and 312 are used to measure magnetoencephalography (MEG) signals. In some embodiments, the magnetic field sensors 302 and 312 are used to measure magnetocardiography (MCG) signals. In some embodiments, multiple types of signals (e.g., MEG signals and MCG signals) measured by the magnetic field sensors 302 and 312 are analyzed collectively.

In some embodiments, the magnetic field sensors 302 and 312 are coupled with flux concentrators 306 and 316 (e.g., magnetic flux concentrators). The flux concentrators 306 and 316 facilitate the detection of magnetic field by the magnetic field sensors 302 and 312 (e.g., by directing the magnetic field toward the magnetic field sensors 302 and 312 or intensifying the magnetic field).

FIGS. 3A and 3B also show that, in some embodiments, the device includes at least two magnetic field sensors 302 and 312. This allows concurrently measurement of magnetic fields from both left and right ears of a subject. However, in some embodiments, the device may include one or more magnetic field sensors for only one ear (e.g., the device may include only one magnetic field sensor).

In FIGS. 3A and 3B, the magnetic field sensor 302 is electrically coupled to a signal analyzer 308. In some embodiments, the signal analyzer includes one or more processors 332, and the magnetic field sensor 302 is electrically coupled (directly or indirectly) to the one or more processors 332. The one or more processors 332 process (e.g., analyze) electrical signals from the magnetic field sensor 302. In some embodiments, the one or more processors 332 are electrically coupled to the magnetic field sensor 302 through one or more additional components, such as an analog-to-digital converter, one or more signal filters 320, etc. The one or more signal filters 320 may filter noises in signals from the magnetic field sensor 302.

When the device includes the magnetic field sensor 312, the magnetic field sensor 312 is also electrically coupled to the one or more processors 332 so that the one or more processors 332 also process (e.g., analyze) electrical signals from the magnetic field sensor 312. In some embodiments, the one or more processors 332 are electrically coupled to the magnetic field sensor 312 through one or more additional components, such as one or more signal filters 322. The one or more signal filters 322 may filter noises in signals from the magnetic field sensor 312.

In configurations with both magnetic field sensors 302 and 312, the device may include combiner circuitry 330. The combiner circuitry 330 may generate electrical signals based on both electrical signals from the magnetic field sensor 302 and electrical signals from the magnetic field sensor 312. For example, the combiner circuitry 330 may generate a sum (or a weighted sum) of the electrical signals from the magnetic field sensor 302 and the electrical signals from the magnetic field sensor 312, a different between the electrical signals from the magnetic field sensor 302 and the electrical signals from the magnetic field sensor 312, etc. In some embodiments, the combiner circuitry 330 combines the electrical signals from the magnetic field sensor 302 and the electrical signals from the magnetic field sensor 312 without summing or subtracting the electrical signals (e.g., both the electrical signals from the magnetic field sensor 302 and the electrical signals from the magnetic field sensor 312 are encoded).

In some embodiments, the one or more processors 332 are electrically coupled with memory 334, which stores instructions for execution by the one or more processors 332.

In some embodiments, the one or more processors 332 are electrically coupled with one or more audio sensors (e.g., a microphone), such as audio sensors 326 and 336. The audio sensors may be used to detect audio signals provided to the ears. By collecting audio signals with the one or more audio sensors, the one or more processors 332 may analyze correlation to changes in the magnetic signals measured by the magnetic field sensors 302 and 312 and changes in the audio signals measured by the audio sensors 326 and 336 (e.g., changes in a brain function in response to certain audio signals). For example, a delayed response to the audio signal may indicate degradation of cognitive functions (e.g., due to accumulation of iron in brain, dementia, or Alzheimer's). In some other cases, the response time to the audio signal may be used to determine athletic ability of a subject. In some cases, the blood flow within adjacent arteries is also measured and compared.

In some embodiments, the one or more processors 332 are electrically coupled to a sound generator 328 (e.g., a speaker) for generating sound. For example, the sound generator 328 may generate audio signals that are provided to the subject to induce a response from the subject (e.g., changes in the brain function). In some cases, the audio signals include signals or instructions causing the subject to perform certain cognitive tasks.

By performing the measurements over a period of time, the changes in the brain response may be recorded. The changes in the brain response may indicate improvement or decline in the brain function (or other related changes, such as accumulation of iron in the brain). In some cases, monitoring the changes in the brain response allows detection of an early onset of brain degenerative diseases.

Figure 4:
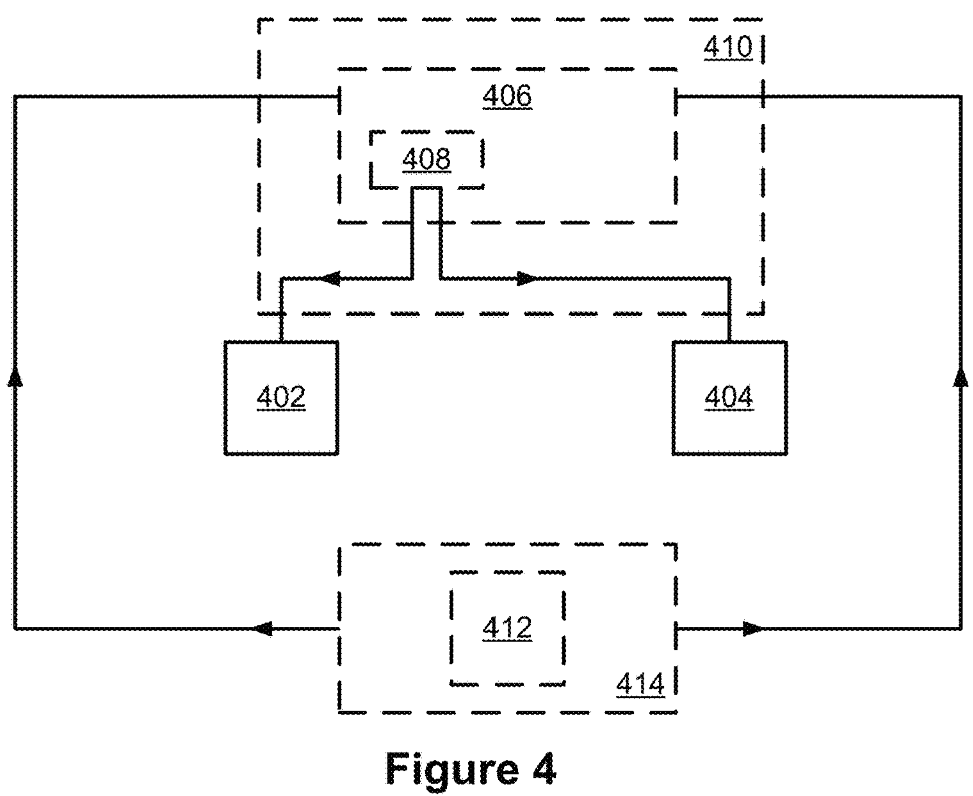
FIG. 4 is a schematic diagram illustrating an electrical connection among selected organs.

FIG. 4 is a schematic diagram illustrating an electrical connection among selected organs.

In FIG. 4, a brain 406 includes multiple portions, such as a basal ganglia, which includes caudate nucleus, globus pallidus, putamen, substantia nigra, and subthalamic nucleus. Portion 408 of the brain 406 represents a portion associated with auditory function of the brain 406. The portion 408 is neurologically connected with the left ear 402 and the right ear 404. Although the neurological connection between a respective ear (e.g., the left ear 402 or the right ear 404) and the portion 408 may provide audio signals from the ear to the portion 408, in some cases, certain signals (e.g., changes in the bio-signals) reflecting the brain function are provided through the connection between the portion 408 and the ear. Thus, the cognitive load 410 from a region including the brain 406 may be detected from the ears 402 and 404.

In addition, biological signals from the chest region 414 (e.g., heart 412) affect the function of the brain 406. For example, the pulse wave velocity path from the heart 412 to the left ear 402 and the pulse wave velocity path from the heart 412 to the right ear 404 may differ. By analyzing the magnetic signals measured from the left and right ears 402 and 404, the changes in the heart function and/or the pulse wave velocity paths can be detected.

Figure 5:
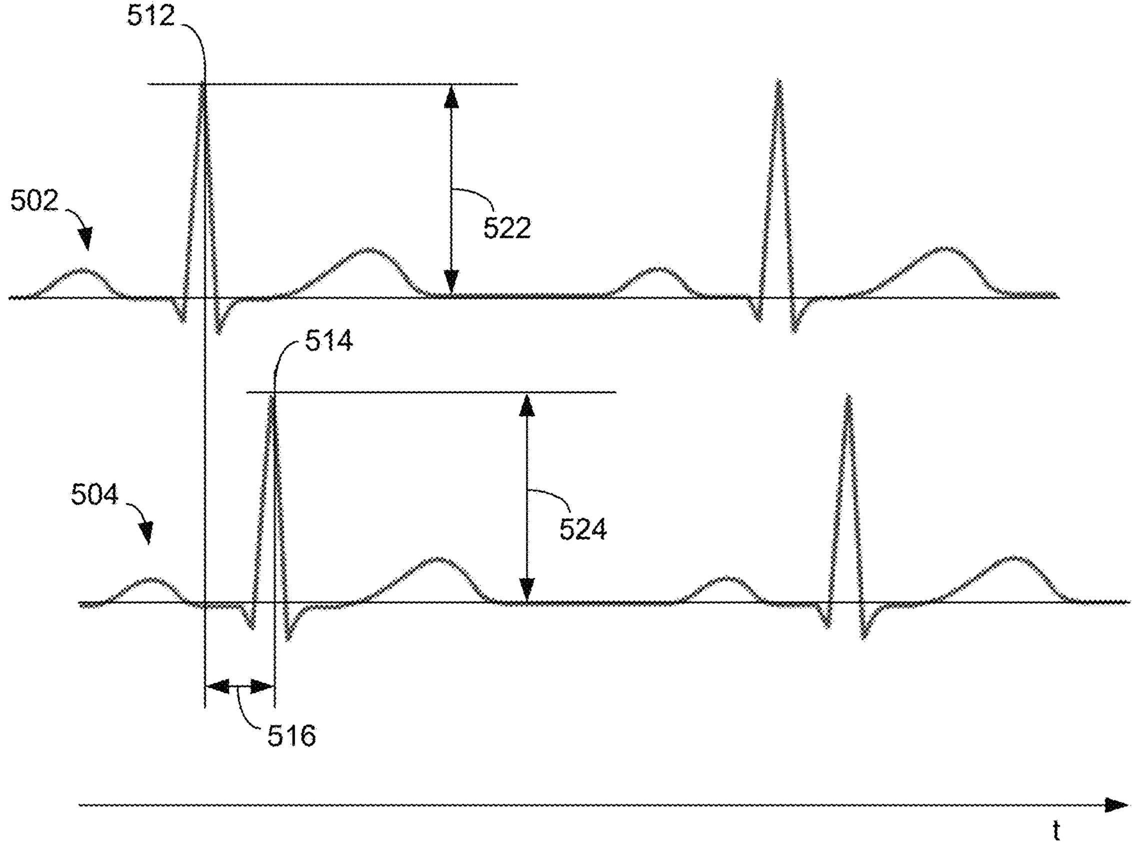
FIG. 5 is a schematic diagram illustrating example electromagnetic signals detected by devices shown in FIG. 3A or 3B.

FIG. 5 is a schematic diagram illustrating example electromagnetic signals detected by devices shown in FIG. 3A or 3B.

The top portion of FIG. 5 shows electromagnetic signals 502 detected by the magnetic field sensor 302 and the bottom portion of FIG. 5 shows electromagnetic signals 504 detected by the magnetic field sensor 312 over time. In FIG. 5, the electromagnetic signals 502 and the electromagnetic signals 504 are vertically offset for clarity. In some embodiments, the electromagnetic signals 502 and the electromagnetic signals 504 are characterized by amplitude and phase. For example, the electromagnetic signals 502 may include a peak 512 with an amplitude 522 and the electromagnetic signals 504 may include a peak 514 with an amplitude 524. In some cases, the amplitude 522 and the amplitude 524 are identical. In some cases, the amplitude 522 and the amplitude 524 are different from each other. In some cases, the difference between the amplitude 522 and the amplitude 524 indicates different attenuation for the electromagnetic signals detected from the left ear and the right ear. FIG. 5 also shows that there is a time difference 516 (or lag) between the peak 512 and the peak 514. In some cases, the time difference between the peak 512 and the peak 514 indicates different delays for the electromagnetic signals detected from the left ear and the right ear. For example, the differences between the peak 512 and the peak 514 (in their amplitudes and/or phases) may indicate different attenuations and delays in the pulse wave velocity paths (to the left ear and the right ear).

Figure 6:
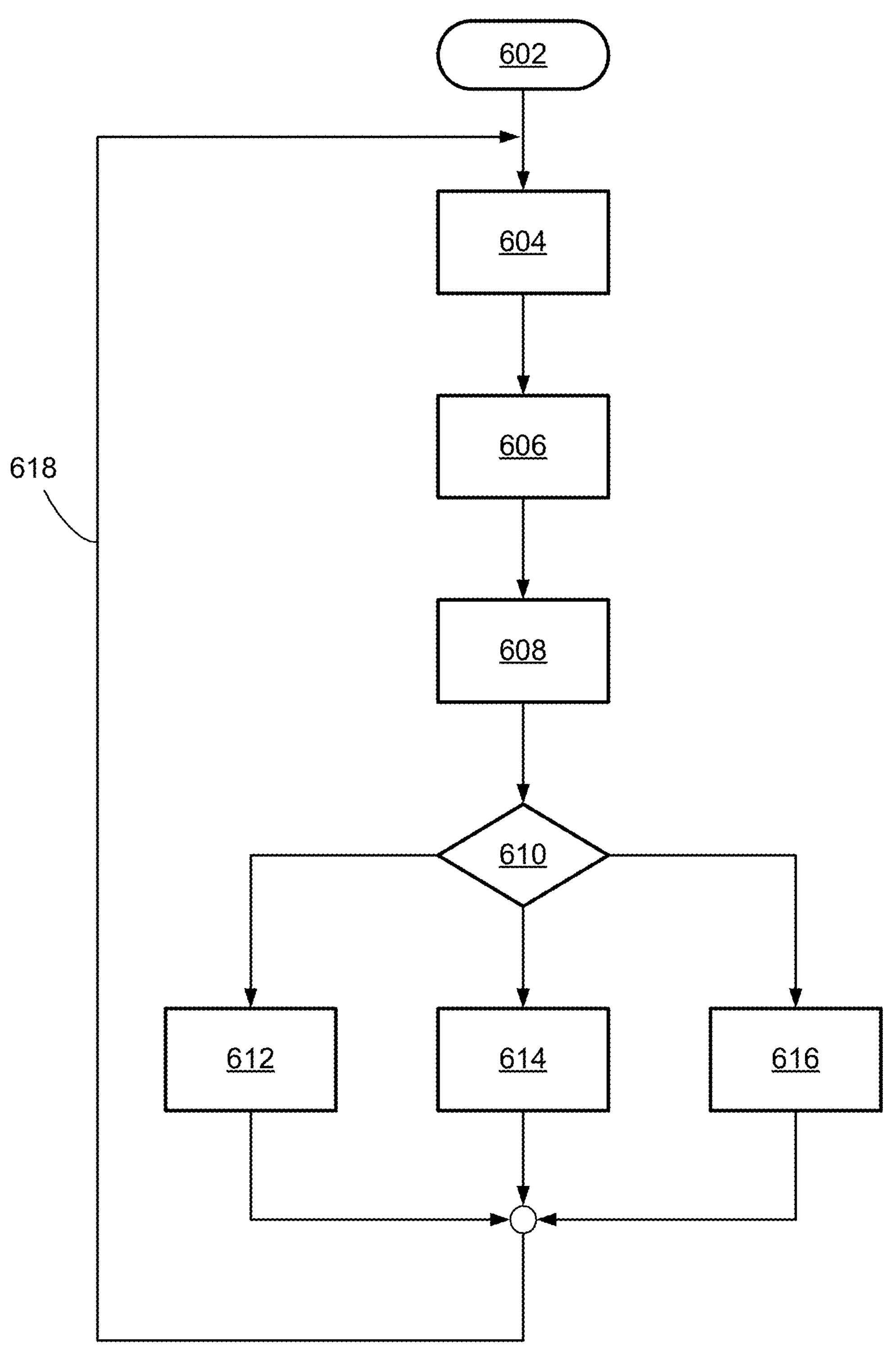
FIG. 6 is a flow diagram illustrating a method of obtaining and processing electromagnetic signals from ear cavities in accordance with some embodiments.

FIG. 6 is a flow diagram illustrating a method of obtaining and processing electromagnetic signals from ear cavities in accordance with some embodiments.

In some embodiments, the method (602) starts by placing the magnetic field sensors adjacent to left and right ears of a subject.

In some embodiments, the method includes (604) measuring electromagnetic signals from a first ear (e.g., a left ear or a right ear) (e.g., using the device shown in FIG. 3A or 3B). In some cases, the strength of the magnetic field ranges between 1 μT and 1 pT.

In some embodiments, the method includes (606) measuring electromagnetic signals from a second ear (e.g., the other ear of the left ear or the right ear that has not been measured in operation 604) (e.g., using the device shown in FIG. 3A or 3B).

In some embodiments, the method includes (608) determining a difference between the electromagnetic signals measured from the left ear and the electromagnetic signals measured from the right ear. In some embodiments, the method includes determining a phase difference between the electromagnetic signals measured from the left ear and the electromagnetic signals measured from the right ear. In some embodiments, the method includes determining an amplitude difference between the electromagnetic signals measured from the left ear and the electromagnetic signals measured from the right ear.

Although FIG. 6 illustrates sequential steps of operation 604 and operation 606, in some embodiments, operation 604 and operation 606 are performed concurrently (e.g., the electromagnetic signals from both ears are measured concurrently).

In some embodiments, the method includes (610) comparing the phase difference and/or the amplitude difference against threshold values.

In some embodiments, the method includes, in accordance with a determination that the left channel has an imbalance (e.g., the electromagnetic signals from the left ear have a lower amplitude than the electromagnetic signals from the right ear by more than a threshold value, or the electromagnetic signals from the left ear have a greater delay than the electromagnetic signals from the right ear by more than a threshold value), (612) providing an indication (e.g., displaying a notice or providing a sound) that the left channel has an imbalance.

In some embodiments, the method includes, in accordance with a determination that the left channel and the right channel are balanced (e.g., the amplitude difference between the electromagnetic signals from the right ear and the electromagnetic signals from the left ear is less than a threshold value, or the phase difference between the electromagnetic signals from the right ear and the electromagnetic signals from the left ear is less than a threshold value), (614) providing an indication (e.g., displaying a notice or providing a sound) that the both channels are balanced (or forgo providing the indication).

In some embodiments, the method includes, in accordance with a determination that the right channel has an imbalance (e.g., the electromagnetic signals from the right ear have a lower amplitude than the electromagnetic signals from the left ear by more than a threshold value, or the electromagnetic signals from the right ear have a greater delay than the electromagnetic signals from the left ear by more than a threshold value), (616) providing an indication (e.g., displaying a notice or providing a sound) that the right channel has an imbalance.

In some embodiments, the method (618) repeats the process from the operation 604.

In light of these examples and principles explained herein, we now turn to certain embodiments.

In accordance with some embodiments, a device includes a first magnetoresistance sensor (e.g., the magnetic field sensor 302) for detecting a magnetic field from a first ear cavity (e.g., a left ear cavity).

In some embodiments, the device also includes a first magnetically shielding enclosure (e.g., enclosure 304) coupled with the first magnetoresistance sensor. The first magnetoresistance sensor is positioned at least partially in the first enclosure (e.g., the magnetic field sensor 302 shown in FIG. 3A or 3B).

In some embodiments, the first magnetoresistance sensor is positioned entirely within the first enclosure (e.g., the magnetic field sensor 302 shown in FIG. 3B). The first enclosure has an opening (e.g., the opening 305) through which the first magnetoresistance sensor detects a change in the magnetic field adjacent to the opening of the first enclosure.

In some embodiments, at least a portion of the first magnetoresistance sensor is positioned outside the first enclosure (e.g., FIG. 3A).

In some embodiments, the device also includes one or more signal filters (e.g., filter 320) for filtering noises in signals from the first magnetoresistance sensor.

In some embodiments, the device also includes a first flux concentrator (e.g., flux concentrator 306) coupled with the first magnetoresistance sensor.

In some embodiments, the device also includes a second magnetoresistance sensor (e.g., the magnetic field sensor 312) for detecting a magnetic field from a second ear cavity.

In some embodiments, the device also includes a second magnetically shielding enclosure (e.g., the enclosure 314) coupled with the second magnetoresistance sensor. The second magnetoresistance sensor is positioned at least partially in the second enclosure (e.g., the magnetic field sensor 312 shown in FIG. 3A or 3B).

In some embodiments, the second magnetoresistance sensor is positioned entirely within the second enclosure (e.g., FIG. 3B). The second enclosure has an opening (e.g., the opening 315) through which the second magnetoresistance sensor detects a change in the magnetic field adjacent to the opening of the second enclosure.

In some embodiments, at least a portion of the second magnetoresistance sensor is positioned outside the second enclosure (e.g., FIG. 3A).

In some embodiments, the device also includes one or more signal filters for filtering noises in signals from the second magnetoresistance sensor (e.g., filter 322).

In some embodiments, the device also includes a second flux concentrator coupled with the second magnetoresistance sensor (e.g., flux concentration 316).

In some embodiments, the device also includes one or more processors (e.g., one or more processors 332) coupled with the first magnetoresistance sensor and the second magnetoresistance sensor, and memory (e.g., memory 334) storing instructions for execution by the one or more processors. The stored instructions including instructions for: receiving, from the first magnetoresistance sensor, first signals indicating the magnetic field from the first ear cavity (e.g., operation 604); receiving, from the second magnetoresistance sensor, second signals indicating the magnetic field from the second ear cavity (e.g., operation 606); and comparing the magnetic field from the first ear cavity and the magnetic field from the second ear cavity by comparing the first signals and the second signals (e.g., operations 608 and 610).

In some embodiments, the stored instructions include instructions for determining a delay between the first signals and the second signals (e.g., time difference 516).

In some embodiments, the stored instructions include instructions for: determining a peak amplitude of the first signals (e.g., amplitude 522); determining a peak amplitude of the second signals (e.g., amplitude 524); and comparing the peak amplitude of the first signals and the peak amplitude of the second signals.

In accordance with some embodiments, a method includes placing a first magnetoresistance sensor adjacent to a first ear cavity; and detecting a magnetic field from the first ear cavity.

In some embodiments, the method also includes placing a second magnetoresistance sensor adjacent to a second ear cavity; and detecting a magnetic field from the second ear cavity.

In some embodiments, the magnetic field from the first ear cavity and the magnetic field from the second ear cavity are concurrently detected.

In some embodiments, the method also includes comparing the magnetic field from the first ear cavity and the magnetic field from the second ear cavity.

In some embodiments, the method also includes extracting at least one of: magnetoencephalography signals or magnetocardiography signals from the detected magnetic field.

Some embodiments may be described with respect to the following clauses:

Clause 1. A device, comprising:

a first magnetoresistance sensor for detecting a magnetic field from a first ear cavity.

Clause 2. The device of clause 1, further comprising:

a first magnetically shielding enclosure coupled with the first magnetoresistance sensor, wherein the first magnetoresistance sensor is positioned at least partially in the first enclosure.

Clause 3. The device of clause 2, wherein:

the first magnetoresistance sensor is positioned entirely within the first enclosure; and the first enclosure has an opening through which the first magnetoresistance sensor detects a change in the magnetic field adjacent to the opening of the first enclosure.

Clause 4. The device of clause 2, wherein:

at least a portion of the first magnetoresistance sensor is positioned outside the first enclosure.

Clause 5. The device of any of clauses 1-4, further comprising:

one or more signal filters for filtering noises in signals from the first magnetoresistance sensor.

Clause 6. The device of any of clauses 1-5, further comprising:

a first flux concentrator coupled with the first magnetoresistance sensor.

Clause 7. The device of any of clauses 1-6, further comprising: a second magnetoresistance sensor for detecting a magnetic field from a second ear cavity.

Clause 8. The device of clause 7, further comprising:

a second magnetically shielding enclosure coupled with the second magnetoresistance sensor, wherein the second magnetoresistance sensor is positioned at least partially in the second enclosure.

Clause 9. The device of clause 8, wherein:

the second magnetoresistance sensor is positioned entirely within the second enclosure; and the second enclosure has an opening through which the second magnetoresistance sensor detects a change in the magnetic field adjacent to the opening of the second enclosure.

Clause 10. The device of clause 8, wherein:

at least a portion of the second magnetoresistance sensor is positioned outside the second enclosure.

Clause 11. The device of any of clauses 7-10, further comprising:

one or more signal filters for filtering noises in signals from the second magnetoresistance sensor.

Clause 12. The device of any of clauses 7-11, further comprising:

a second flux concentrator coupled with the second magnetoresistance sensor.

Clause 13. The device of any of clauses 7-12, further comprising:

one or more processors coupled with the first magnetoresistance sensor and the second magnetoresistance sensor; and memory storing instructions for execution by the one or more processors, the stored instructions including instructions for:

receiving, from the first magnetoresistance sensor, first signals indicating the magnetic field from the first ear cavity;

receiving, from the second magnetoresistance sensor, second signals indicating the magnetic field from the second ear cavity; and comparing the magnetic field from the first ear cavity and the magnetic field from the second ear cavity by comparing the first signals and the second signals.

Clause 14. The device of clause 13, wherein:

the stored instructions include instructions for determining a delay between the first signals and the second signals.

Clause 15. The device of clause 13 or 14, wherein:

the stored instructions include instructions for:

determining a peak amplitude of the first signals;

determining a peak amplitude of the second signals; and comparing the peak amplitude of the first signals and the peak amplitude of the second signals.

Clause 16. A method, comprising:

placing a first magnetoresistance sensor adjacent to a first ear cavity; and detecting a magnetic field from the first ear cavity.

Clause 17. The method of clause 16, further comprising:

placing a second magnetoresistance sensor adjacent to a second ear cavity; and detecting a magnetic field from the second ear cavity.

Clause 18. The method of clause 17, wherein:

the magnetic field from the first ear cavity and the magnetic field from the second ear cavity are concurrently detected.

Clause 19. The method of clause 17 or 18, further comprising:

comparing the magnetic field from the first ear cavity and the magnetic field from the second ear cavity.

Clause 20. The method of any of clauses 16-19, further comprising:

extracting at least one of: magnetoencephalography signals or magnetocardiography signals from the detected magnetic field.

The foregoing description, for purpose of explanation, has been described with reference to specific embodiments. However, the illustrative discussions above are not intended to be exhaustive or to limit the scope of claims to the precise forms disclosed. Many modifications and variations are possible in view of the above teachings. The embodiments were chosen and described in order to best explain the principles of the various described embodiments and their practical applications, to thereby enable others skilled in the art to best utilize the principles and the various described embodiments with various modifications as are suited to the particular use contemplated.

What is claimed is:

1. An ear-based brain function monitoring device, comprising:

a first magnetoresistance sensor positioned within a first enclosure and configured for detecting a magnetic field to measure magnetoencephalography (MEG) signals from a first ear cavity of a user, the magnetic field containing indications of brain function of the user;

the first enclosure configured to magnetically shield the first magnetoresistance sensor from environmental magnetic noise, wherein the first enclosure has an opening through which the magnetic field from the first ear cavity enters the first enclosure to be detected by the first magnetoresistance sensor;

a second magnetoresistance sensor positioned within a second enclosure and configured for detecting a second magnetic field from a second ear cavity, the second magnetic field containing second indications of the brain function of the user; and one or more processors coupled with the first magnetoresistance sensor and the second magnetoresistance sensor; and memory storing instructions for execution by the one or more processors, the stored instructions including instructions for:

receiving, from the first magnetoresistance sensor, first signals indicating the magnetic field from the first ear cavity;

receiving, from the second magnetoresistance sensor, second signals indicating the second magnetic field from the second ear cavity;

comparing the magnetic field from the first ear cavity and the second magnetic field from the second ear cavity by comparing the first signals and the second signals; and monitoring the brain function of the user based on the comparing.

2. The device of claim 1, wherein the first magnetoresistance sensor is positioned entirely within the first enclosure.

3. The device of claim 1, wherein at least a portion of the first magnetoresistance sensor is positioned outside the first enclosure.

4. The device of claim 1, further comprising one or more signal filters for filtering noises in signals from the first magnetoresistance sensor.

5. The device of claim 1, further comprising a first flux concentrator coupled with the first magnetoresistance sensor.

6. The device of claim 1, wherein:

the second magnetoresistance sensor is positioned entirely within the second enclosure; and the second enclosure has an opening through which the second magnetoresistance sensor detects a change in the second magnetic field.

7. The device of claim 1, wherein at least a portion of the second magnetoresistance sensor is positioned outside the second enclosure.

8. The device of claim 1, further comprising one or more signal filters for filtering noises in signals from the second magnetoresistance sensor.

9. The device of claim 1, further comprising a second flux concentrator coupled with the second magnetoresistance sensor.

10. The device of claim 1, wherein the stored instructions include instructions for determining a delay between the first signals and the second signals.

11. The device of claim 1, wherein the stored instructions include instructions for:

determining a peak amplitude of the first signals;

determining a peak amplitude of the second signals; and comparing the peak amplitude of the first signals and the peak amplitude of the second signals.

12. The device of claim 1, further comprising a sound generator configured to generate audio signals that are provided to the user to induce a response from the user that is measurable by the first magnetoresistance sensor.

* * * * *